United States Patent
Miki et al.

(10) Patent No.: US 8,410,435 B2
(45) Date of Patent: Apr. 2, 2013

(54) CYCLONE SEPARATOR TYPE MASS ANALYZING SYSTEM

(75) Inventors: Shinichi Miki, Chofu (JP); Michisato Toyoda, Suita (JP)

(73) Assignees: MSI. Tokyo, Inc., Tokyo (JP); Osaka University, Osaka (JP)

( * ) Notice: Subject to any disclaimer, the term of this patent is extended or adjusted under 35 U.S.C. 154(b) by 0 days.

(21) Appl. No.: 13/376,840

(22) PCT Filed: Jun. 9, 2010

(86) PCT No.: PCT/JP2010/003853
§ 371 (c)(1),
(2), (4) Date: Dec. 8, 2011

(87) PCT Pub. No.: WO2010/143426
PCT Pub. Date: Dec. 16, 2010

(65) Prior Publication Data
US 2012/0080593 A1    Apr. 5, 2012

(30) Foreign Application Priority Data
Jun. 10, 2009 (JP) ................. 2009-138922

(51) Int. Cl.
*H01J 49/04* (2006.01)
(52) U.S. Cl. ......... 250/288; 250/281; 250/282; 250/289
(58) Field of Classification Search .................. 250/281, 250/282, 288, 289
See application file for complete search history.

(56) References Cited

U.S. PATENT DOCUMENTS

| | | | | | |
|---|---|---|---|---|---|
| 4,092,130 | A | * | 5/1978 | Wikdahl | 95/34 |
| 4,108,620 | A | * | 8/1978 | Bohme et al. | 96/397 |
| 2010/0000943 | A1 | * | 1/2010 | Carson et al. | 210/638 |

FOREIGN PATENT DOCUMENTS

| | | | |
|---|---|---|---|
| JP | 58-223737 | A | 12/1983 |
| JP | 7-55689 | A | 3/1995 |
| JP | 7-294393 | A | 11/1995 |
| JP | 9-145568 | A | 6/1997 |
| JP | 2000-214149 | A | 8/2000 |
| JP | 2001-183284 | A | 7/2001 |
| JP | 2002-543975 | A | 12/2002 |
| JP | 2006150167 | A * | 6/2006 |
| JP | 2008-224246 | A | 9/2008 |

OTHER PUBLICATIONS

Iternational Search Report for PCT/JP2010/003853 from the Japanese Patent Office completed on Jul. 2, 2010 and mailed Jul. 13, 2010 (4 pages).

* cited by examiner

*Primary Examiner* — Michael Logie
(74) *Attorney, Agent, or Firm* — Pyprus pte Ltd (57) ABSTRACT

Provided is a small-sized mass analysis system capable of analyzing an analysis target system being under atmospheric pressure. The mass analysis system (7) has a cyclone separator (1) including a hollow shaft motor (19) for rotationally driving a turbo blade (17). Combining a mass analysis device with the cyclone separator makes it possible to remove dust and introduce into the mass analysis device a gas present in a region where the pressure in the cyclone separator is sufficiently reduced.

5 Claims, 9 Drawing Sheets

CYCLONE SEPARATOR TYPE MASS ANALYZING SYSTEM

BACKGROUND OF THE INVENTION

1. Field of the Invention

The present invention relates to a cyclone separator type mass analyzing system capable of removing dust from a gas containing the dust and performing a mass analysis of a gas in a vacuum system.

2. Description of the Related Art

In recent years, there has been a rising interest in the safety or the environment. For this reason, there is a demand for an apparatus capable of analyzing toxic substances suspended in an atmosphere in real time with high sensitivity.

As analysis apparatuses for a gas, a liquid, and a solid, a mass analyzing apparatus is known. In particular, a mass analyzing apparatus that has a vacuum system is known as mass analyzing apparatus for analyzing mass of a target gas. The mass analyzing apparatus can analyze the substances contained in the target gas. However, the mass analyzing apparatus needs to keep a high state of vacuum. For this reason, when the atmosphere is directly introduced into the mass analyzing apparatus, the analysis precision may be degraded and the inside of the vacuum device may be contaminated.

Japanese Patent Application Laid-Open (JP-A) No. 2008-224246 discloses a particle mass spectrometry. Further, JP-A No. H 07-55689 discloses a particle mass spectrometer. In the particle mass spectrometers disclosed in JP-A Nos. 2006-224246 and H 07-55689, an aerosol is introduced through an aerosol intake pipe, and a gas having plural types of particles suspended therein is classified according to each particle having a predetermined range of a ratio mass (mass of particle/charge), thereby obtaining a particle mass distribution.

SUMMARY OF THE INVENTION

However, even when such a particle mass spectrometer is used, the atmosphere may not be effectively analyzed. This is because the atmosphere contains much dust. For this reason, when the atmosphere is introduced into the particle mass spectrometer, the inside of the vacuum chamber is contaminated, and the analysis precision is degraded. Also, since a small hole (an orifice) used for differential exhaust is blocked, it is difficult to stably operate the mass analyzing apparatus. As a method which does not introduce dust into a vacuum, a method may be supposed in which a filter is installed at the front stage of a vacuum chamber. However, when a fine filter is used, not only dust but also a target gas for analysis may be absorbed and attached to the inside of the filter. For this reason, the mass analyzing apparatus equipped with the fine filter is not appropriate for the real-time analysis. Meanwhile, fine powders may not be removed in a rough filter.

In this case, a method may be supposed in which a low-vacuum chamber and a middle-vacuum chamber are connected in a tandem manner to the front side of an aerosol intake pipe of a particle mass spectrometer and a gas is introduced into a mass analyzing apparatus after a differential exhaust is performed and the vacuum degree thereof is gradually increased. However, in such a differential exhaust system, the apparatus is great in size.

Therefore, it is an object of the invention to provide a small mass analyzing system capable of analyzing an analysis subject system under the atmospheric pressure.

Basically, the invention is based on knowledge that a gas, from which dust is removed and of which a pressure is sufficiently reduced, may be introduced into a mass analyzing apparatus by combining a cyclone separator with a mass analyzing apparatus. In particular, the invention is based on knowledge that the atmosphere may be adjusted to a state in which the atmosphere may be directly introduced into the mass analyzing apparatus by using a swirl generating device 13 which is configured by the combination of a turbo blade 17 and a hollow motor 19.

A first aspect of the invention relates to a mass analyzing system 7 that has: a cyclone separator 1; an analyzing apparatus introduction port 3 that is attached to the cyclone separator 1; and a mass analyzing apparatus 5 that is connected to the cyclone separator 1 through the analyzing apparatus introduction port 3.

In addition, the cyclone separator 1 has a swirl generating container 9, an intake port 11 that is attached to the swirl generating container 9 and is used to take a gas into the swirl generating container 9, a swirl generating device 13 that swirls the gas taken into the swirl generating container 9, and an exhaust port 15 that discharges a gas rotationally separated in the gas taken into the swirl generating container 9. The mass analyzing apparatus 5 further has a vacuum system.

The swirl generating device 13 has a turbo blade 17 and a hollow motor 19 that rotationally drives the turbo blade 17. The turbo blade 17 is provided so that the rotation center of the turbo blade 17 is coaxial with the center of the analyzing apparatus introduction port 3. The pressure of the atmosphere may be adjusted to a state in which the atmosphere may be introduced directly into the mass analyzing apparatus 5 by using the swirl generating device 13 configured by the combination of the turbo blade 17 and the hollow motor 19. That is, with such a configuration, the mass analyzing system of the invention may introduce a gas, from which dust is removed and of which a pressure is sufficiently reduced, into the mass analyzing apparatus 5.

A second aspect of the invention relates to a method of analyzing a substance contained in a gas. The method comprises: rotationally separating a target gas contained in a gas by a cyclone separator 1; introducing the rotationally separated target gas into a mass analyzing apparatus 5; and analyzing a mass of a substance contained in the target gas introduced into the mass analyzing apparatus 5.

The rotationally separating of the target gas comprises ionizing the target gas contained in the gas and accumulating the ionized target gas at the center portion of the cyclone separator 1 by swirling the target gas contained in the gas and disposing an ion source portion, which may be ionized under the atmospheric pressure through electrospray or discharge ionization, in the swirling gas.

In the introducing of the rotationally separated gas into the mass analyzing apparatus 5, the target gas, which is in a low-pressure state due to the rotationally separating of the target gas and is ionized and accumulated at the center portion of the cyclone separator 1, is introduced into the mass analyzing apparatus 5.

The invention may introduce a gas, which is present in an area where dust is removed by the cyclone separator and the pressure inside the cyclone separator is sufficiently reduced, into the mass analyzing apparatus by combining the cyclone separator with the mass analyzing apparatus. Accordingly, an analysis subject system under the atmospheric pressure may be analyzed. Furthermore, since a pump for the differential exhaust is not needed, the mass analyzing apparatus may be decreased in size. For this reason, although the existing mass analyzing apparatus does not have portability, according to the aspects of the invention, an atmospheric mass analyzing apparatus which has portability may be provided.

BRIEF DESCRIPTION OF THE DRAWINGS

FIGS. 5A to 5C are diagrams illustrating an example of a cyclone separator and an analyzing apparatus introduction port: FIG. 50 is an exploded diagram;

DETAILED DESCRIPTION OF EMBODIMENTS

Figure 1:
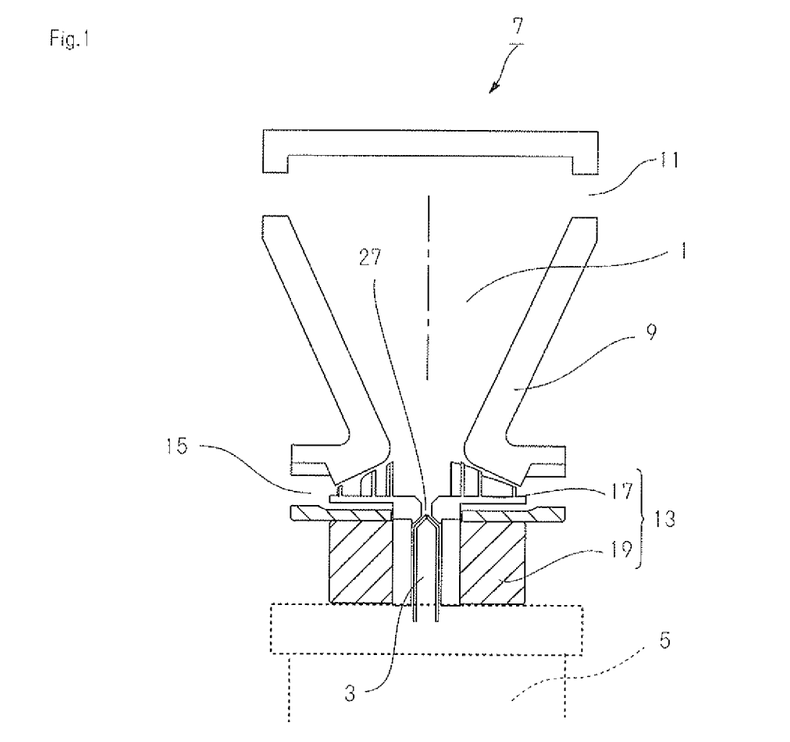
FIG. 1 is a schematic diagram illustrating the configuration of a mass analyzing system of the invention.

FIG. 1 is a schematic diagram illustrating the configuration of a mass analyzing system of the invention. As illustrated in FIG. 1, the mass analyzing system of the invention has a cyclone separator 1, an analyzing apparatus introduction port 3, and a mass analyzing apparatus 5. In the mass analyzing system of the invention, the cyclone separator 1 is connected to the mass analyzing apparatus 5 through the analyzing apparatus introduction port 3 which is attached to the cyclone separator 1.

As illustrated in FIG. 1, the cyclone separator 1 has a swirl generating container 9, an intake port 11, a swirl generating device 13, and an exhaust port 15.

The swirl generating container 9 is a container which causes a gas to swirl therein. In a case where a liquid or a solid is charged in the swirl generating container 9, the swirl generating container 9 may swirl the liquid or the solid. As the swirl generating container 9, a swirl generating container which is used in the cyclone separator may be used. With regard to the detailed configuration of the swirl generating container 9, as illustrated in FIG. 1, the swirl generating container has a trumpet-like inner wall of which the diameter becomes smaller as it moves downward. The swirl generating container 9 may be produced from the same material as that of a vacuum chamber. Furthermore, it is desirable to hermetically seal the swirl generating container 9 by a cover portion.

The intake port 11 is attached to the swirl generating container 9, and is used to take a gas into the swirl generating container 9. It is desirable to install the intake port 11 at the upper portion of the swirl generating container 9. One intake port 11 may be attached to the swirl generating container 9 or two or more intake ports may be provided. In a case where a plurality of the intake ports 11 is attached to the swirl generating container 9, it is desirable to provide the intake ports 11 at the positions symmetrical to each other with the swirl generating container 9 interposed therebetween. A filter may be appropriately installed at the intake portion of the intake port 11. Since the intake port 11 has the filter, comparatively large trash may be removed. Accordingly, it is possible to prevent an accident in which large matters or living bodies (for example, insects) enter the swirl generating container 9.

The intake port 11 may be a pipe which has a circular cross-section. In this case, the diameter of the cross-section may be from 1 cm to 10 cm.

Figure 2:
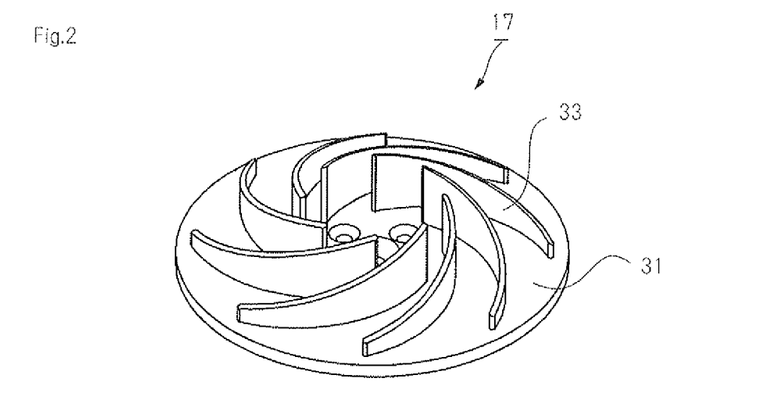
FIG. 2 is a diagram illustrating an example of a turbo blade of the invention.

The swirl generating device 13 is a device which swirls the gas taken into the swirl generating container 9. Furthermore, in a case where a liquid or a solid is charged in the swirl generating container 9, the swirl generating container may swirl them. The swirl generating device 13 may include a turbo blade 17 and a hollow motor 19 which rotationally drives the turbo blade 17. In addition, the turbo blade 17 is provided so that the rotation center of the turbo blade 17 is coaxial with that of the analyzing apparatus introduction port 3. The turbo blade 17 has already known as disclosed in Japanese Patent No. 3637021. FIG. 2 is a diagram illustrating an example of the turbo blade of the invention. As illustrated in FIG. 2, the turbo blade 17 of the invention has a disk-like rotation plate 31 and a plurality of vanes 33 which is installed on the rotation plate 31. The plurality of vanes is provided so as to be symmetrical to each other with respect to the center of the rotation plate. In order to form a spiral air stream inside the swirl generating container 9, it is desirable to arrange the plurality of vanes so that it is not arranged in a radial shape, but is bent in a predetermined direction. Further, as illustrated in FIG. 2, it is desirable that the plurality of vanes have a portion of which the height from the substrate becomes higher as it moves closer to the center of the rotation plate. Since the turbo blade 17 has such a shape, the spiral air stream may be effectively generated inside the swirl generating container 9. It is desirable that the turbo blade 17 of the invention have a hole portion formed at the center of the substrate. In addition, it is desirable that the analyzing apparatus introduction port 3 be installed at the hole portion of the substrate with the hole portion. For example, the size of the hole portion of the substrate may be set such that the diameter is from 0.1 mm to 10 mm or from 0.4 mm to 2 mm. Further, the rotationally separated gas may be guided to a discharge port through the gap between the turbo blade 17 and the swirl generating container 9. The hollow motor 19 is a motor which has a hollow penetration hole. In the mass analyzing system 7 of the invention, it is desirable to install the analyzing apparatus introduction port 3 inside the penetration hole. For example, the diameter of the penetration hole may be from 0.1 mm to 10 mm or from 0.4 mm to 2 mm. For example, the rotation speed of the hollow motor 19 may be 40,000 rpm or more.

The exhaust port 15 is a portion which discharges the rotationally separated gas in the gas which is taken in,o the swirl generating container 9. Furthermore, in a case where a liquid or a solid is charged in the swirl generating container 9, the exhaust port 15 is used to discharge the liquid or the solid. That is, the exhaust port serves as a discharge port.

The analyzing apparatus introduction port 3 is a portion which connects the cyclone separator 1 to the mass analyzing apparatus 5. An example of the analyzing apparatus introduction port 3 has a gas pipe with an orifice. The analyzing apparatus introduction port 3 may be configured to introduce the gas inside the cyclone separator into the mass analyzing apparatus 5 through the hole provided at the center of the substrate of the turbo blade 17 and the penetration hole of the hollow motor 19.

In addition, the mass analyzing apparatus 5 of the invention is a mass analyzing apparatus with a vacuum system. The invention relates to the mass analyzing apparatus which may be used as various types of mass analyzing apparatuses. Examples of the mass analyzing apparatus include a time-of-flight type, an ion-trap type, a quadrupole type, an FT-ICR type, a magnetic field type, and an ion mobility spectrometry (IMS) type. Among these examples, the time-of-flight type mass analyzing apparatus may be desirably used in the invention. The mass analyzing apparatus 5 with a vacuum system maintains the inside of the chamber at a high vacuum degree. For this reason, it is difficult to directly analyze the gas contained in the atmosphere. In the invention, the portion of the gas, from which dust is removed by using the cyclone separator 1 and of which the pressure is low at the swirling center, is introduced into the mass analyzing apparatus 5. Accordingly, although a simple apparatus is provided, the apparatus may introduce the gas under the atmospheric pressure thereinto and analyze the elements of the gas.

As a desirable example of the mass analyzing apparatus, a mass analyzing apparatus is disclosed in Japanese Patent No. 4208674, JP-A No. 2005-79049, or JP-A No. 11-135060. The example of the mass analyzing apparatus is a "time-of-flight type mass spectrometer having an input orbit for ion implanting and an output orbit for ion extracting installed in a closed orbit formed by a plurality of sector electrical fields". In general, the time-of-flight type mass spectrometer has a plurality of vacuum chambers and a plurality of pumps, and has a size of 1 m or more. Thus, generally, the time-of-flight type mass spectrometer is installed in a laboratory. The time-of-flight type mass spectrometer disclosed in Japanese Patent No. 4208674, JP-A No. 2005-79049, or JP-A No. 11-135060 may be decreased in size so that it may be carried. Thus, when the time-of-flight type mass spectrometer is combined with the mass analyzing system of the invention, a portable mass analyzing system may be obtained. Accordingly, there is no need to sample a gas and analyze the gas in the laboratory. Specifically, for example, when a user brings the mass analyzing system of the invention to the desired observation site, the local atmosphere may be analyzed in real time.

Figure 3:
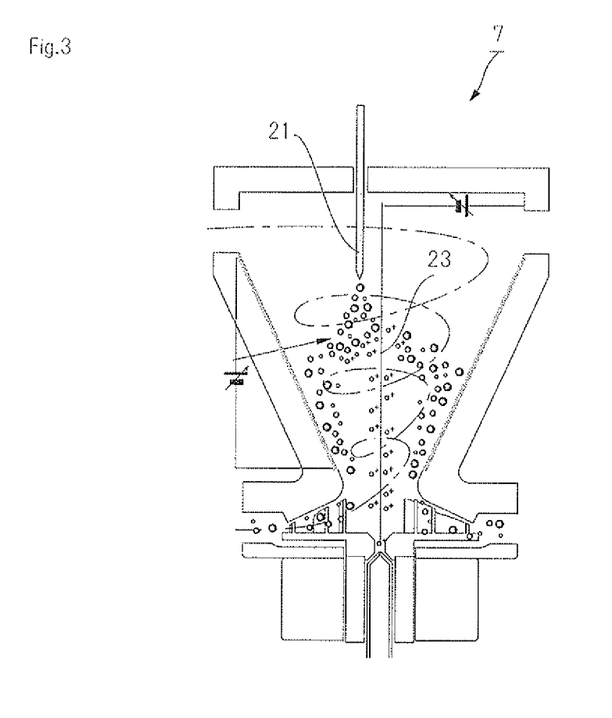
FIG. 3 is a schematic diagram illustrating the mass analyzing system which has an ionization portion and a guide wire.

FIG. 3 is a schematic diagram illustrating the mass analyzing system including an ionization portion and a guide wire. As illustrated in FIG. 3, the mass analyzing system 7 has an ionization portion 21 and a guide wire 23. In addition, the ionization portion 21 is installed inside the swirl generating container 9, and is used to ionize the gas which is taken into the swirl generating container 9. The ionization portion 21 may be implemented as an available ionization portion if it may ionize the gas taken into the swirl generating container 9. Examples of specific ionization method include atmospheric ionization, electrospray ionization, fast atom bombardment ionization, electron ionization, chemical ionization, electrolyte desorption ionization, and electrolyte ionization. In the invention, since it is an object to attract the charged target gas molecules to the guide wire 23, atmospheric ionization or electrospray ionization may be desirably used as the ionization method.

The guide wire 23 is disposed so as to be coaxial with the analyzing apparatus introduction port 3 inside the swirl generating container 9, and is used to attract a gas ionized by the ionization portion 21. For this reason, it is desirable that the guide wire 23 have a charging property. Further, it is desirable that the mass analyzing system 7 have a voltage supply which is used to apply a potential to the guide wire 23.

As another desirable type of the mass analyzing system 7, an electrical discharge portion 25 is installed inside the swirl generating container 9.

Figure 4:
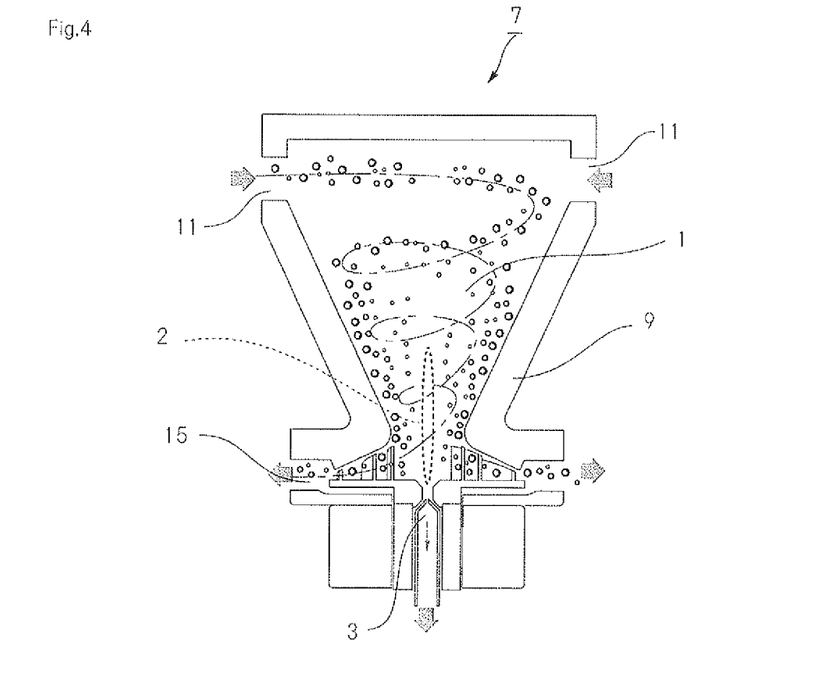
FIG. 4 is a conceptual diagram showing a shape in which the mass analyzing system of the invention is operated.

Next, the operational example of the mass analyzing system 7 of the invention will be described. FIG. 4 is a conceptual diagram illustrating a shape in which the mass analyzing system of the invention is operated. The mass analyzing system 7 of the invention may be used for a method of analyzing a substance contained in a gas. In addition, the method comprises: rotationally separating a target gas contained in a gas by the cyclone separator 1; introducing the rotationally separated target gas into the mass analyzing apparatus 5; and analyzing the mass of the substance contained in the target gas which is introduced into the mass analyzing apparatus 5.

The rotationally separating of the target gas contained in the gas using the cyclone separator 1 will be described. An example of the gas is an atmosphere. The gas in the specification may include not only a gas, but also a solid such as fine powder like the atmosphere. The turbo blade 17 rotates inside the swirl generating container 9, so that a spiral air stream is generated as illustrated in FIG. 3. In addition, the gas is introduced from the intake port 11 into the swirl generating container 9. Then, the introduced gas moves downward in a swirling manner. At this time, since heavy substance undergoes a strong centrifugal force, the heavy substance performs a large swirling motion. Meanwhile, since the light substance does not undergo a strong centrifugal force, the light substance performs a comparatively small swirling motion. In this way, the heavy substance is separated to the outside and the light substance is separated to the inside due to the centrifugal force. Accordingly, the gas is centrifugally separated by the specific weight thereof. The gas having a heavy specific weight is guided to the exhaust port 15 and is discharged to the outside. On the other hand, the swirling motion becomes violent as it moves downward. As a result, a pressure reduction area is formed at the lower center portion of the cyclone separator 1. That is, the gas having a light specific weight is accumulated at the center portion of the cyclone separator 1 so that the pressure is reduced due to the rotationally separating. The pressure reduction area 2 is illustrated in the drawing. The pressure reduction area 2 is generated at the center portion of the mass analyzing system 7 of the invention by using the cyclone separator 1. In particular, the portion of the pressure reduction area 2 near the mass analyzing apparatus becomes a low vacuum state.

Furthermore, the mass analyzing system 7 which has the ionization portion 21 and the guide wire 23 ionizes the gas contained inside the swirl generating container 9. The charge which is opposite to the ionization charge is applied to the guide wire 23. For example, when the gas is negatively ionized, the guide wire 23 is positively charged. Then, the ionized gas is attracted to the guide wire 23 and is accumulated near the center of the cyclone separator 1.

In the introducing of the rotationally separated gas into the mass analyzing apparatus 5, the gas of which the pressure is reduced and which is accumulated at the center portion of the cyclone separator 1 by the rotationally separating is introduced into the mass analyzing apparatus 5. That is, since the center portions of the turbo blade 17 and the hollow motor 19 are hollow and are coaxial with the swirling center of the gas, the gas from which dust or the like is removed and of which the pressure is reduced may be introduced into the mass analyzing apparatus 5.

Furthermore, the mass analyzing apparatus has been described so far in which the analyzing apparatus introduction port 3 and the mass analyzing apparatus 5 are installed at the downstream area where the gas taken from the intake port 11 swirls. However, the analyzing apparatus introduction port 3 may be installed near the intake port 11. In this case, molecules (including excited molecules) or ions are emitted from the downstream area. In addition, the molecules or. ions emitted from the emitting portion of the downstream area cause an interaction with the gas which is taken from the intake port 11 and is rotationally separated. In addition, the gas which has been subjected to the interaction is taken from the analyzing apparatus introduction port 3.

An example of the emitting portion has a direct analysis in real time (DART) ion source. Such a DART (registered trademark) ion source is disclosed in, for example, the specifications of Japanese Patent Application National Publication No. 2006-523367, US Patent No. 6949741, and JP-A No. 2007-256246. The entire content of such cited documents is incorporated herein by reference.

The DART method is atmospheric ionization which uses excited gas molecules (atoms) without charges. In this method, excited molecules produced by corona discharge or glow discharge are made to cause a reaction with a sample under the atmospheric pressure so that the sample is ionized, and the ionized sample is introduced into an ion introduction port (an orifice) of a mass spectrometer.

More than anything else, in the invention, the reduced pressure state is desirable instead of the atmospheric pressure state. That is, the preferred mass analyzing system of the invention has a pressure reducing mechanism which reduces the pressure inside the ion source or the swirl generating container 9. An example of the pressure reducing mechanism has a pump. As a result of the pressure reduction, the pressure may be from 0.1 atm to 0.9 atm or from 0.2 atm to 0.5 atm. In the invention, since it is desirable to maintain the electrical discharge inside the swirl generating container 9, it is desirable to conduct the reaction under the reduced pressure. In particular, when the reaction is conducted under the reduced pressure, the use of an expensive helium gas may be suppressed. Thus, a cheap gas, for example, a nitrogen gas may be used as a substituted gas.

Embodiment 1

Figure 5A:
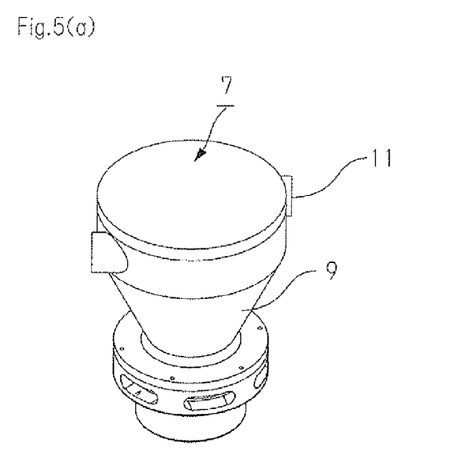
FIG. 5A is a front perspective view.
Figure 5B:
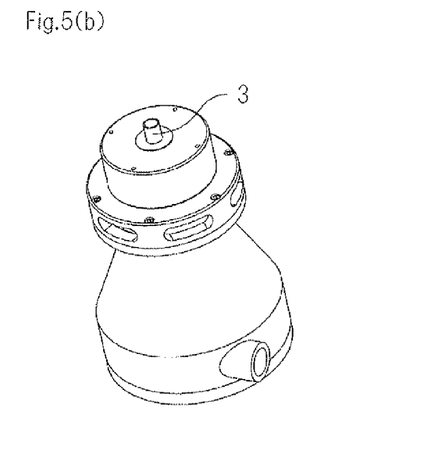
FIG. 5B is a bottom perspective view.
Figure 5C:
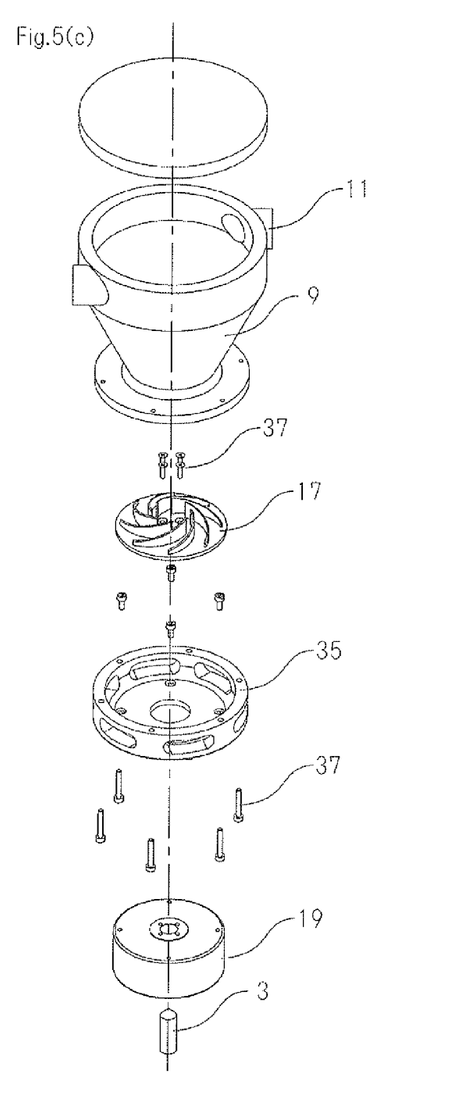

Embodiment 1 relates to a mass analyzing system which analyzes elements contained in the atmosphere. FIGS. 5A to 5C are diagrams illustrating an example of the cyclone separator and the analyzing apparatus introduction port. FIG. 5A is a front perspective view, FIG. 5B is a bottom perspective view, and FIG. 5C is an exploded diagram. As illustrated in FIGS. 5A to 5C, the cyclone separator 1 has the swirl generating container 9, the intake port 11, the swirl generating device 13 (the turbo blade 17 and the hollow motor 19), and the exhaust port 15 (the dust exhaust port). As illustrated in FIG. 5C, the hollow motor 19 is fixed to the swirl generating container 9 by a connecting flange. The front end of the analyzing apparatus introduction port 3 near the swirl generating container 9 is tapered, so that an orifice is formed. Furthermore, the mass analyzing apparatus is omitted in FIGS. 5A to 5C. The cyclone separator 1 and the analyzing apparatus introduction port 3 illustrated in FIGS. 5A to 5C are connected to the mass analyzing apparatus and constitute the mass analyzing system 7. In the drawings, the connecting flange 35 and the fixation screw 37 are provided.

Embodiment 2

Figure 6:
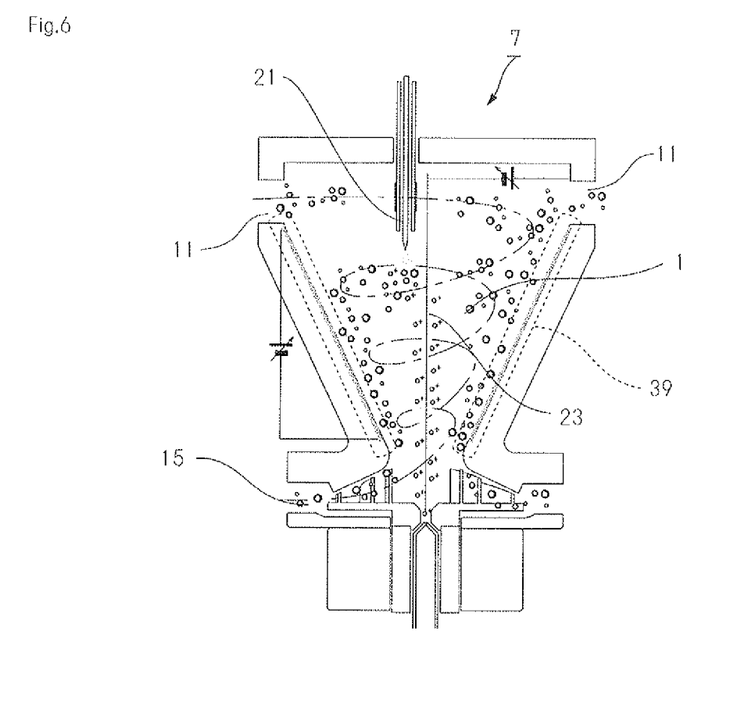
FIG. 6 is a schematic diagram illustrating the mass analyzing system which has the ionization portion and the guide wire.

Embodiment 2 relates to a mass analyzing system which has an ionization portion and a guide wire. FIG. 6 is a schematic diagram illustrating the mass analyzing system which has the ionization portion and the guide wire. The guide wire is a wire which is formed of a conductive material. In this example, the ionization is conducted by atmospheric ionization so that the gas introduced into the swirl generating container 9 becomes, for example, a negative ion. In addition, an inner wall 39 of the swirl generating container 9 is formed as a high resistor. A voltage is applied to the inner wall and the guide wire 23. Then, a potential difference occurs between the inner wall and the guide wire 23. Accordingly, an electric field is generated inside the swirl generating container 9. At this time, a voltage is applied so that the guide wire 23 is positively charged. Then, the ionized gas swirls while being attracted to the guide wire 23. With such a configuration, dust or the like which is not easily ionized is not accumulated at the center portion. For this reason, dust or the like may be effectively centrifugally separated.

Embodiment 3

Figure 7:
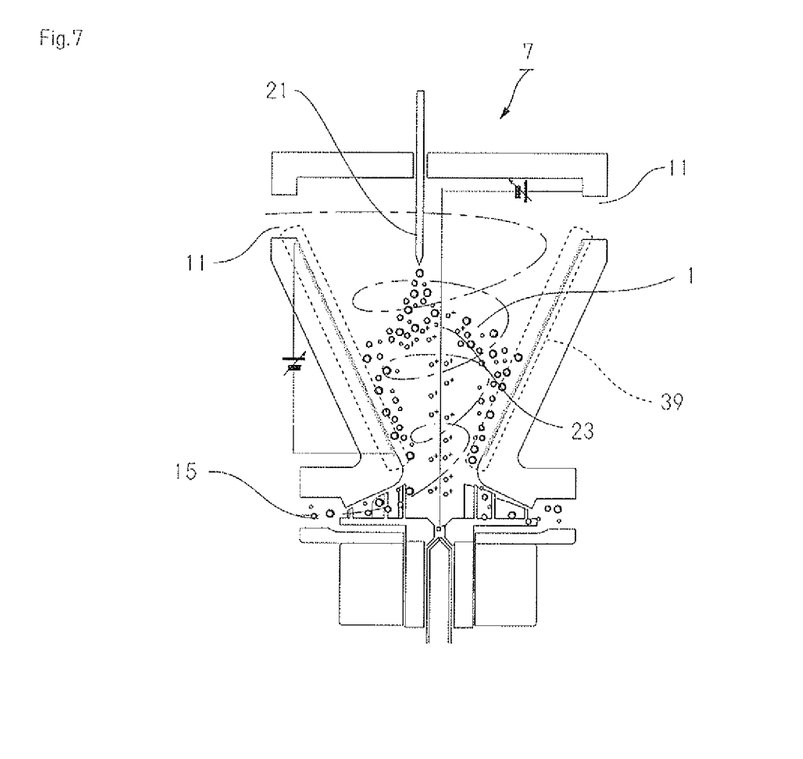
FIG. 7 is a schematic diagram illustrating the mass analyzing system which uses electrospray as an ionization method.

Embodiment 3 relates to a mass analyzing system which uses electrospray as an ionization method. FIG. 7 is a schematic diagram illustrating the mass analyzing system which uses electrospray as an ionization method. In this system, a nitrogen gas is introduced from the intake port 11 into the swirl generating container 9. Meanwhile, an analysis subject substance is made as a solution, and is sprayed by using the introduced nitrogen gas. Coulomb explosion is caused during the process of drying the liquid droplet, and ions are produced. The liquid droplet swirls due to the air stream inside the swirl generating container 9. Then, the liquid droplet is actively dried. In addition, the large liquid droplet which does not change into an ion is centrifugally separated and is guided to the exhaust port 15. When the liquid droplet is introduced into the mass analyzing apparatus 5, the vacuum degree of the mass analyzing apparatus 5 may not be maintained and the inside of the mass analyzing apparatus is contaminated. In the mass analyzing system 7 of the embodiment, since only the liquid droplet changed into a gas and an ion may be introduced into the mass analyzing apparatus, the burden of the vacuum system may be reduced. Further, as described above, the ionized gas may be accumulated near the guide wire 23 and the selection efficiency may be improved by using the guide wire.

Embodiment 4

Figure 8:
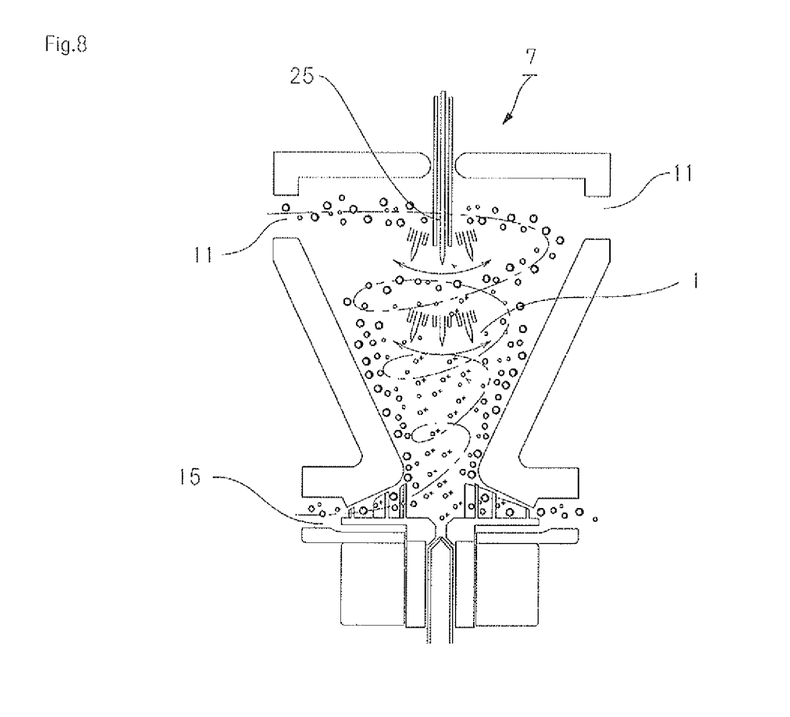
FIG. 8 is a schematic diagram illustrating the mass analyzing system which has an electrical discharge portion inside the swirl generating container.

Embodiment 4 relates to a mass analyzing system which has an electrical discharge portion 25 inside the swirl generating container 9. FIG. 8 is a schematic diagram illustrating the mass analyzing system which has the electrical discharge portion inside the swirl generating container. As illustrated in FIG. 8, in the example of the system, a discharge probe is provided as the electrical discharge portion 25. The inert gas is excited by causing an electrical discharge in the discharge probe. The excited inert gas is made to collide with the analysis subject substance. Then, charges are exchanged between the inert gas and the analysis subject substance. The mass of the produced ion is much smaller than that of dust. For this reason, the produced ion moves downward while swirling the vicinity of the center portion, and is guided from the center portion of the turbo blade 17 to the mass analyzing apparatus 5 through the orifice Embodiment 5

Figure 9:
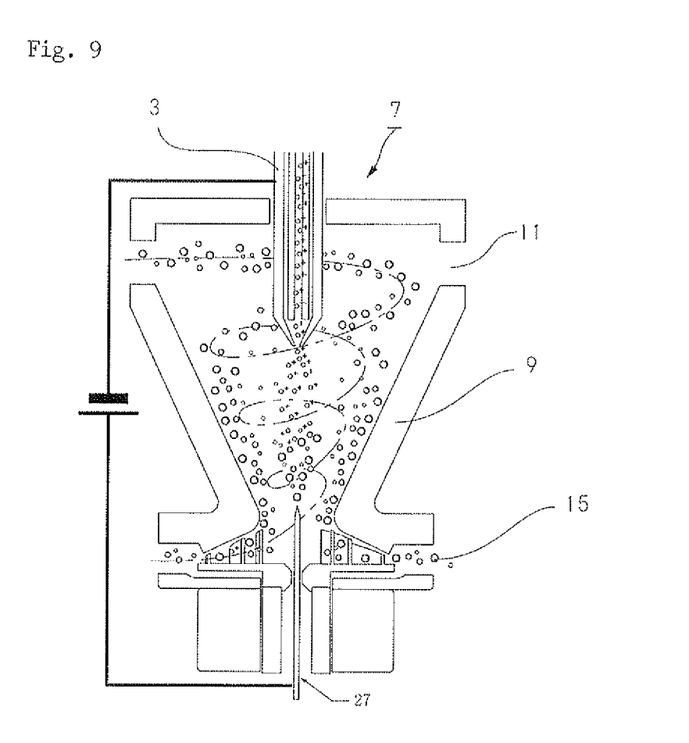
FIG. 9 is a diagram illustrating the mass analyzing system of Embodiment 5.

Embodiment 5 relates to a mass analyzing system in which the analyzing apparatus introduction port 3 is positioned at the upstream area of the molecule stream instead of the downstream from the intake port 11. With regard to the detailed configuration of the mass analyzing system, the above-described configuration may be appropriately employed. FIG. 9 is a diagram illustrating the mass analyzing system of Embodiment 5. The mass analyzing system further has an emitting portion 27 which is provided inside the swirl generating container 9 so as to emit molecules or ions from the swirl generating device 13. Specifically, the mass analyzing system has the emitting portion 27 which passes the rotary shaft of the swirl generating device 13. An example of the emitting portion 27 has an electrospray or a spray needle. In addition, ions or molecules (including excited molecules) are sprayed or emitted along the center axis of the hollow motor which constitutes the swirl generating device 13. In this case, the analyzing apparatus introduction port 3 is provided at a position facing the emitting portion 27.

The mass analyzing system of the invention may be effectively used in the field relating to an analytical instrument.

REFERENCE SIGNS LIST 1 cyclone separator
3 analyzing apparatus introduction port
5 mass analyzing apparatus
7 mass analyzing system
9 swirl generating container
11 intake port
13 swirl generating device
15 exhaust port
17 turbo blade
19 hollow motor
21 ionization portion
23 guide wire
25 electrical discharge portion
27 emitting portion

What is claimed is:

1. A mass analyzing system (7) comprising:
a cyclone separator (1);
an analyzing apparatus introduction port (3) that is attached to the cyclone separator (1); and
a mass analyzing apparatus (5) that is connected to the cyclone separator (1) through the analyzing apparatus introduction port (3),
wherein the cyclone separator (1) comprises:
a swirl generating container (9);
an intake port (11) that is attached to the swirl generating container (9) and is used to take a gas into the swirl generating container (9),
a swirl generating device (13) that swirls the gas taken into the swirl generating container (9), and
an exhaust port (15) that discharges a gas rotationally separated in the gas taken into the swirl generating container (9),
wherein the mass analyzing apparatus (5) comprises a vacuum system,
wherein the swirl generating device (13) comprises a turbo blade (17) and a hollow motor (19) that rotationally drives the turbo blade (17), and
wherein the turbo blade (17) is provided so that the rotation center of the turbo blade (17) is coaxial with the center of the analyzing apparatus introduction port (3).

2. The mass analyzing system according to claim 1, further comprising:
an ionization portion (21); and
a guide wire (23),
wherein the ionization portion (21) is provided inside the swirl generating container (9) and is used to ionize the gas taken into the swirl generating container (9), and
wherein the guide wire (23) is provided so as to be coaxial with the analyzing apparatus introduction port (3) inside the swirl generating container (9) and is used to attract the gas ionized by the ionization portion (21).

3. The mass analyzing system according to claim 1, further comprising:
an electrical discharge portion (25) that is installed inside the swirl generating container (9).

4. The mass analyzing system according to claim 1, further comprising:
an emitting portion (27) that is installed inside the swirl generating container (9) so as to emit molecules or ions from the swirl generating device (13),
wherein the analyzing apparatus introduction port (3) is installed at a position facing the emitting portion (27).

5. A method of analyzing a substance contained in a gas, the method comprising:
rotationally separating a target gas contained in a gas by a cyclone separator (1);
introducing the rotationally separated target gas into a mass analyzing apparatus (5); and
analyzing a mass of a substance contained in the target gas introduced into the mass analyzing apparatus (5),
wherein the rotationally separating of the target gas comprises ionizing the target gas contained in the gas and accumulating the ionized target gas at the center portion of the cyclone separator (1) by swirling the target gas contained in the gas, and
wherein in the introducing of the rotationally separated gas into the mass analyzing apparatus (5), the target gas, which is in a low-pressure state due to the rotationally separating of the target gas and is ionized and accumulated at the center portion of the cyclone separator (1), is introduced into the mass analyzing apparatus (5).

* * * * *